United States Patent [19]

Velenyi

[11] Patent Number: 4,808,563
[45] Date of Patent: Feb. 28, 1989

[54] MOLYBDENUM-TUNGSTEN-CONTAINING CATALYST FOR METHANE CONVERSION PROCESS

[75] Inventor: Louis J. Velenyi, Lyndhurst, Ohio

[73] Assignee: The Standard Oil Company, Cleveland, Ohio

[21] Appl. No.: 87,534

[22] Filed: Aug. 19, 1987

Related U.S. Application Data

[62] Division of Ser. No. 843,095, Mar. 24, 1986, Pat. No. 4,695,668.

[51] Int. Cl.[4] .................. B01J 21/08; B01J 23/02; B01J 23/28; B01J 23/30
[52] U.S. Cl. .................. 502/241; 502/63; 502/64; 502/65; 502/66; 502/178; 502/183; 502/184; 502/185; 502/206; 502/242; 502/243; 502/246; 502/247; 502/248; 502/250; 502/255; 502/302; 502/303; 502/304; 502/306; 502/308; 502/309; 502/310; 502/311; 502/312; 502/313; 502/314; 502/317; 502/319; 502/320; 502/321; 502/322
[58] Field of Search .............. 502/312, 321, 322, 63, 502/64, 65, 66, 178, 183, 184, 185, 206, 241, 242, 243, 246, 247, 248, 250, 255, 302, 303, 304, 306, 308, 309, 310, 311, 313, 314, 317, 319, 320

[56] References Cited

U.S. PATENT DOCUMENTS

| | | | |
|---|---|---|---|
| Re. 29,901 | 2/1979 | Wada et al. | 252/443 |
| 1,958,648 | 5/1934 | Steigerwald | 260/168 |
| 2,211,219 | 8/1940 | Thacker | 260/683 |
| 2,859,258 | 11/1958 | Fischer et al. | 260/683 |
| 3,810,954 | 5/1974 | Bertus | 260/680 E |
| 3,857,796 | 12/1974 | Takenaka et al. | 502/312 |
| 4,042,533 | 8/1977 | Shaw et al. | 502/312 X |
| 4,170,570 | 10/1979 | Zagata et al. | 252/437 |
| 4,172,810 | 10/1979 | Mitchell et al. | 252/465 |
| 4,205,194 | 5/1980 | Mitchell et al. | 585/500 X |
| 4,239,658 | 12/1980 | Mitchell et al. | 252/465 |
| 4,250,054 | 2/1981 | Shaw et al. | 502/312 X |
| 4,250,346 | 2/1981 | Young et al. | 585/658 |
| 4,279,777 | 7/1981 | Velenyi et al. | 252/439 |
| 4,443,647 | 4/1984 | Jones et al. | 585/500 |
| 4,450,310 | 5/1984 | Fox et al. | 585/400 |
| 4,523,049 | 6/1985 | Jones et al. | 585/500 |

FOREIGN PATENT DOCUMENTS 7409013 1/1975 Netherlands ............ 502/312

Primary Examiner—W. J. Shine
Attorney, Agent, or Firm—Raymond F. Keller; David J. Untener; Larry W. Evans

[57] ABSTRACT

A catalyst is disclosed which comprises a molybdenum-tungsten-containing complex represented by the formula $$Mo_a W_b M_c A_d O_e$$

wherein M is selected from the group consisting of one or more metals selected from any of Groups IB, IIB, IVB, VB or VIII of the Periodic Table and/or one or more of Y, Cr, Mn, Re, B, In, Ge, Sn, Pb, Th or U, or a mixture of two or more of the metals in said group; A is at least one metal selected from the group consisting of alkali metals, alkaline earth metals, Lanthanide series metals, La, Tl, or a mixture or two or more of the metals in said group; a is a number in the range of from about 1 to about 200; b is a number in the range of from about 1 to about 200; with the proviso that either Mo or W is in excess of the other, the ratio of a:b being about 4:1 or greater, or about 1:4 or less; c is a number such that the ratio of c:(a+b) is in the range of from 0:100 to about 10:100; d is a number such that the ratio of d:(a+b) is in the range of from 0:100 to about 75:100; and e is the number of oxygens needed to fulfill the valence requirements of the other elements. A process for converting gaseous reactants comprising methane and oxygen to higher order hydrocarbons using the foregoing catalyst is also disclosed.

15 Claims, No Drawings

MOLYBDENUM-TUNGSTEN-CONTAINING CATALYST FOR METHANE CONVERSION PROCESS

This is a divisional of co-pending application Ser. No. 843,095 filed on 3/24/86, now U.S. Pat. No. 4,695,668.

TECHNICAL FIELD

This invention relates to a molybdenum-tungsten-containing catalyst and to a process for converting methane to higher order hydrocarbons using said catalyst. The process is particularly suitable for converting methane to ethane, ethylene and mixtures thereof.

BACKGROUND OF THE INVENTION

The term "higher order hydrocarbon" refers to a hydrocarbon having at least two carbon atoms.

A major source of methane is natural gas. Primary sources for natural gas are the porous reservoirs generally associated with crude oil reserves. From these sources come most of the natural gas used for heating purposes. Quantities of natural gas are also known to be present in coal deposits and are by-products of crude oil refinery processes and bacterial decomposition of organic matter. Natural gas obtained from these sources is generally utilized as a fuel at the site.

Prior to commercial use, natural gas must be processed to remove water vapor, condensible hydrocarbons and inert or poisonous constituents. Condensible hydrocarbons are generally removed by cooling natural gas to a low temperature and then washing the natural gas with a cold hydrocarbon liquid to absorb the condensible hydrocarbons. The condensible hydrocarbons are typically ethane and heavier hydrocarbons. This gas processing can occur at the wellhead or at a central processing station. Processed natural gas typically comprises a major amount of methane, and minor amounts of ethane, propane, the butanes, the pentanes, carbon dioxide and nitrogen. Generally, processed natural gas comprises from about 50% to more than about 95% by volume of methane.

Most processed natural gas is distributed through extensive pipeline distribution networks. As natural gas reserves in close proximity to gas usage decrease, new sources that are more distant require additional transportation. Many of these distant sources are not, however, amendable to transport by pipeline. For example, sources that are located in areas requiring economically unfeasible pipeline networks or in areas requiring transport across large bodies of water are not amendable to transport by pipeline. This problem has been addressed in several ways. One such solution has been to build a production facility at the site of the natural gas deposit to manufacture one specific product. This approach is limited as the natural gas can be used only for one product, preempting other feasible uses. Another approach has been to liquefy the natural gas and transport the liquid natural gas in specially designed tanker ships. Natural gas can be reduced to 1/600th of the volume occupied in the gaseous state by such processing, and with proper procedures, safely stored or transported. These processes, which involve liquefying natural gas to a temperature of about $-162°$ C., transporting the gas, and revaporizing it are complex and energy intensive.

Still another approach has been the conversion of natural gas to higher order hydrocarbons that can be easily handled and transported. In this way easily transportable commodities may be derived directly from natural gas at the wellhead. The conversion of natural gas to higher order hydrocarbons, especially ethane and ethylene, retains the material's versatility for use as precursor materials in chemical processing. Known processes are available for the further conversion of ethane and ethylene to other useful materials.

The conversion of methane to higher order hydrocarbons at high temperatures, in excess of about 1200° C. is known. These processes are, however, energy intensive and have not been developed to the point where high yields are obtained even with the use of catalysts. Catalysts that are useful in these processes (e.g., chlorine) are corrosive under such operating conditions.

The catalytic oxidative coupling of methane at atmospheric pressure and temperatures of from about 500° C. to 1000° C. has been investigated by G. E. Keller and M. M. Bhasin. These researchers reported the synthesis of ethylene via oxidative coupling of methane over a wide variety of metal oxides supported on an alpha alumina structure in *Journal of Catalysis*, 73, 9–19 (1982). This article discloses the use of single component oxide catalysts that exhibited methane conversion to higher order hydrocarbons at rates no greater than 4%. The process by which Keller and Bhasin oxidized methane was cyclic, varying the feed composition between methane, nitrogen and air (oxygen) to obtain higher selectivities.

West German Patent DE No. 32370792 discloses the use of single supported component oxide catalysts. The process taught by this reference utilizes low oxygen partial pressure to give a high selectivity for the formation of ethane and ethylene. The conversion of methane to ethane and ethylene is, however, only on the order of from about 4% to about 7%.

Methods for converting methane to higher order hydrocarbons at temperatures in the range of about 500° C. to about 1000° C. are disclosed in U.S. Pat. Nos. 4,443,644; 4,443,645; 4,443,646; 4,443,647; 4,443,648; and 4,443,649. The processes taught by these references provide relatively high selectivities to higher order hydrocarbons but at relatively low conversion rates, on the order of less than about 4% overall conversion. In addition to synthesizing hydrocarbons, the processes disclosed in these references also produced a reduced metal oxide which must be frequently regenerated by contact with oxygen. The preferred processes taught by these references entail physically separate zones for a methane contacting step and for an oxygen contacting step, with the reaction promoter recirculating between the two zones.

U.S. Pat. Nos. 4,172,810; 4,205,194; and 4,239,658 disclose the production of hydrocarbons including ethane, ethylene, propane, benzene and the like, in the presence of a catalyst-reagent composition which comprises: (1) a group VIII noble metal having an atomic number of 45 or greater, nickel, or a group Ib noble metal having an atomic number of 47 or greater; (2) a group VIb metal oxide which is capable of being reduced to a lower oxide; and (3) a group IIa metal selected from the group consisting of magnesium and strontium composited with a passivated, spinel-coated refractory support or calcium composited with a passivated, non-zinc containing spinel-coated refractory support. The feed streams used in the processes disclosed in these references do not contain oxygen. The references indicate that oxygen is avoided for the purposes of avoiding coke formation on the catalyst. Periodic regeneration of the catalysts disclosed in these references is required.

U.S. Pat. No. 4,450,310 discloses a methane conversion process for the production of olefins and hydrogen comprising contacting methane in the absence of oxygen and in the absence of water at a reaction temperature of at least 500° C. with a catalyst comprising the mixed oxides of a first metal selected from lithium, sodium, potassium, rubidium, cesium and mixtures thereof, a second metal selected from beryllium, magnesium, calcium, strontium, barium, and mixtures thereof, and optionally a promoter metal selected from copper, rhenium, tungsten, zirconium, rhodium, and mixtures thereof.

SUMMARY OF THE INVENTION

The present invention provides for a catalyst comprising a molybdenum-tungsten-containing complex represented by the formula $$Mo_aW_bM_cA_dO_e$$

wherein

M is selected from the group consisting of one or more metals selected from any of Groups IB, IIB, IVB, VB or VIII of the Periodic Table and/or one or more of Y, Cr, Mn, Re, B, In, Ge, Sn, Pb, Th or U, or a mixture of two or more of the metals in said group;

A is at least one metal selected from the group consisting of alkali metals, alkaline earth metals, Lanthanide series metals, La, Tl, or a mixture of two or more of the metals in said group;

a is a number in the range of from about 1 to about 200;

b is a number in the range of from about 1 to about 200;

with the proviso that either Mo or W is in excess of the other, the ratio of a:b being about 4:1 or greater, or about 1:4 or less;

c is a number such that the ratio of c:(a+b) is in the range of from 0:100 to about 10:100;

d is a number such that the ratio of d:(a+b) is in the range of from 0:100 to about 75:100; and e is the number of oxygens needed to fulfill the valence requirements of the other elements.

The invention further provides for a process for converting methane to at least one higher order hydrocarbon comprising contacting a gaseous reactant comprising methane and oxygen with the foregoing molybdenum-tungsten-containing catalyst for an effective period of time to provide said higher order hydrocarbon.

DESCRIPTION OF THE PREFERRED EMBODIMENT

Catalyst:

The catalyst of the invention comprises a molybdenum-tungsten-containing complex represented by the formula $$Mo_aW_bM_cA_dO_e$$

wherein

M is selected from the group consisting of one or more metals selected from any of Groups IB (e.g., Cu, etc.), IIB (e.g., Zn, etc.), IVB (e.g., Ti, etc.), VB (e.g., V, etc.) or VIII (e.g., Fe, Co, Ni, etc.) of the Periodic Table and/or one or more of Y, Cr, Mn, Re, B, In, Ge, Sn, Pb, Th or U, or a mixture of two or more of the metals in said group. M is preferably selected from the group consisting of Co, V, Re, Nb, Rh, Ir, Ag, B, Ru, Pt, U, Th, Ti or a mixture of two or more thereof. M is more preferably selected from the group consisting of Co, V, Re, Nb or a mixture of two or more thereof.

A is at least one metal selected from the group consisting of alkali metals (e.g., Li, Na, K, etc.), alkaline earth metals (e.g., Be, Mg, Ca, etc.), Lanthanide series metals (e.g., Ce, Pr, Nd, etc.), La, Tl, or a mixture of two or more of the metals in said group. A is preferably selected from the group consisting of Na, K, Rb, Cs, Mg, Ca, Sr, Ba or a mixture of two or more thereof. A is more preferably selected from the group consisting of K, Na, Cs or a mixture of two or more thereof.

a is a number in the range of from about 1 to about 200. Preferably a is in the range of from about 1 to about 100.

b is a number in the range of from about 1 to about 200. Preferably b is in the range of from about 1 to about 100.

It is a critical feature of this invention that either Mo or W is in excess of the other and that the ratio of a:b be at least about 4:1 or greater, or about 1:4 or less. Preferably the ratio of a:b is in the range of from about 4:1 to about 200:1, more preferably in the range of from about 4:1 to about 100:1. Alternatively, the ratio of a:b is preferably in the range of from about 1:4 to about 1:200, more preferably in the range of from about 1:4 to about 1:100. Without this excess of Mo over W, or W over Mo, the advantageous conversion rates provided for with the inventive process are not possible.

c is a number such that the ratio of c:(a+b) is in the range of from 0:100 to about 10:100, preferably in the range of from about 1:100 to about 5:100, more preferably in the range of from about 1:100 to about 2:100.

d is a number such that the ratio of d:(a+b) is in the range of from 0:100 to about 75:100, preferably in the range of from about 1:100 to about 30:100, more preferably in the range of from about 2:100 to about 10:100.

e is the number of oxygens needed to fulfill the valence requirements of the other elements.

The foregoing or molybdenum-tungsten-containing complex can be formed in any conventional manner, such as tabletting, pelleting, or supporting the active complex material on a carrier. Suitable carrier materials include silica, alumina, fused alumina, zirconia, hafnia, titania, magnesia, germanium oxide, silicon carbide, clay, zeolite or activated carbon. Silica is preferred. In general, the carrier may be employed in amounts of up to about 99.5% by weight of the final catalyst composition. Preferably, the carrier material comprises at least about 75% by weight of the final catalyst composition, more preferably at least about 95%, and advantageously about 98% by weight of the final catalyst composition.

The zeolite can be any zeolite that is suitable for use as a catalytic support material. These zeolites are preferably crystalline, hydrated, framework aluminosilicates which are based on a three-dimensional network of $AlO_4$ and $SiO_4$ tetrahedra linked to each other by sharing all of the oxygens. These zeolites may be represented by the empirical formula $$M_{2/n}O \cdot Al_2O_3 \cdot xSiO_2 \cdot yH_2O$$

wherein, M is a cation, x is generally equal to or greater than 2 since $AlO_4$ tetrahedra are joined only to $SiO_4$ tetrahedra, and n is the cation valence. The framework contains channels and interconnected voids which are occupied by the cation, M, and water molecules. The cations may be mobile and exchangeable to varying degrees by other cations. Ammonium and alkylammonium cations may be incorporated in the zeolites, e.g., $NH_4$, $CH_3NH_3$, $(CH_3)_2NH_2$, $(CH_3)_3NH$, and $(CH_3)_4N$. The structural formula of a zeolite can be expressed for the crystallographic unit cell as $$M_{x/n}[(AlO_2)_x(SiO_2)_y] \cdot wH_2O$$

wherein M is a cation of valence n, w is the number of water molecules and the ratio y/x usually has values of 1–100 depending upon the structure. The sum (x+y) is the total number of tetrahedra in the unit cell. The complex within the [] represents the framework composition. The zeolites described in the patent literature and published journals are usually designated by letters or other convenient symbols. Exemplary of these materials are Zeolite A (U.S. Pat. No. 2,882,243), Zeolite X (U.S. Pat. No. 2,882,244), Zeolite Y (U.S. Pat. No. 3,130,007), Zeolite ZSM-5 (U.S. Pat. No. 3,702,886), Zeolite ZSM-11 (U.S. Pat. No. 3,709,979), and Zeolite ZSM-12 (U.S. Pat. No. 3,832,449). These patents are incorporated herein by reference.

The term "activated carbon" is used herein to refer to an amorphous form of carbon characterized by high adsorptivity for many gases, vapors and colloidal solids. The sources of activated carbon and the techniques for preparing it are well known to those skilled in the art and, accordingly, need not be described in detail herein. Briefly, activated carbon is usually obtained by the destructive distillation of wood, nut shells, animal bones or other carbonaceous material. It is typically "activated" by heating to about 800°–900° C. with steam or carbon dioxide which results in a porous internal structure (honeycomb-like).

The catalysts of the invention may be prepared by coprecipitation or by other methods known in the art. Generally they are prepared by mixing an aqueous solution of compounds containing the metal components, forming a precipitate and drying this precipitate. Examples of the compounds containing the metal components that are useful include but are not limited to oxides, hydroxides, inorganic salts (e.g., nitrates, phosphates, halides, carbonates, silicates, aluminates) and salts of organic acids (e.g., acetates, formates, butyrates, propionates, benzoates and the like). The catalyst may be calcined to produce desirable physical properties such as attrition resistance, optimum surface area and particle size.

The catalyst may be incorporated with the carrier by coating, impregnation or coprecipitation using known techniques. The catalyst can be co-precipitated with one carrier material (e.g., silica) and then the combination of catalyst and carrier can be coated on another carrier material (e.g., Alundum, a product of Norton Co. identified as fused alumina).

A particularly useful coating procedure is disclosed in U.S. Pat. No. 4,077,912, which is incorporated herein by reference. Briefly, this method involves partially wetting the carrier, contacting the partially wetted carrier with a powdered precipitate of the catalytic components, then gently agitating the mixture until the catalytic complex is formed. Agitation is conveniently conducted by placing the partially wetted carrier in a rotating drum and adding the powdered precipitate until none is taken up by the carrier. The liquid used to wet the carrier may include inorganic or organic liquids and is dependent upon the type of catalytic components employed. The liquid and the catalytic components should have a relatively high degree of attraction for each other.

The catalytic components can also be impregnated on the carrier by depositing a solution containing the catalytic components on the carrier using known techniques, then drying and calcining.

The catalytic components may optionally be individually coated or impregnated on a carrier using the above-indicated technique.

In order to further illustrate the preparation of the catalysts of the invention, the following Examples 1–10 are provided. In the following examples as well as throughout the specification and in the appended claims, all parts and percentages are by weight and all temperatures are in degrees centigrade, unless otherwise indicated.

EXAMPLE 1

2% $Mo_{90}WVO_x$/98% $SiO_2$ 25 ml. of concentrated reagent grade $NH_4OH$ were dissolved in 25 ml. of distilled water. 2.0902 gms. of $(NH_4)_6Mo_7O_{24} \cdot 4H_2O$ were added to the mixture with stirring. 0.0156 gm. of $NH_4VO_3$ was added. 0.0309 gm. of $WO_3$ was added. The mixture was heated to a temperature of 95° C. and stirred rapidly for 15 minutes. 221.25 gms. of a 40% by weight colloidal dispersion of $SiO_2$ were added with stirring. The mixture was heated at boiling until near dryness. The mixture was then dried overnight at 110° C., then calcined at 420° C. for 3 hours. The calcined product was cooled to room temperature and then ground to a 10–30 mesh size. This catalyst had a density of 0.504 gm/cc.

EXAMPLE 2

2% $Mo_{90}WCoKO_x$/98% $SiO_2$ 25 ml. of concentrated reagent grade $NH_4OH$ were dissolved in 25 ml. of distilled water. 2.0902 gms. of $(NH_4)_6Mo_7O_{24} \cdot 4H_2O$ were added to the mixture with stirring. 0.0333 gm. of $H_2WO_4$ was added. 0.0388 gm. of $Co(NO_3)_2 \cdot 6H_2O$ was added. 0.0135 gm. of $KNO_3$ was added. The mixture was heated to a temperature of 95° C. and stirred rapidly for 15 minutes. 130.40 gms. of a 40% by weight colloidal dispersion of $SiO_2$ were added with stirring. The mixture was heated at boiling until near dryness. The mixture was then dried overnight at 110° C., then calcined at 420° C. for 3 hours. The calcined product was cooled to room temperature and then ground to a 10–30 mesh size. This catalyst had a density of 0.280 gm/cc.

EXAMPLE 3

2% $W_{90}MoCoO_x$/98% $SiO_2$ 25 ml. of concentrated reagent grade $NH_4OH$ were dissolved in 25 ml. of distilled water. 0.0234 gm. of $(NH_4)_6Mo_7O_{24} \cdot 4H_2O$ was added to the mixture with stirring. 2.9983 gms. of $H_2WO_4$ were added. 0.0388 gm. of $Co(NO_3)_2.6H_2O$ was added. The mixture was heated to a temperature of 95° C. and stirred rapidly for 15 minutes. 206.64 gms. of a 40% by weight colloidal dispersion of $SiO_2$ were added with stirring. The mixture was heated at boiling until near dryness. The mixture was then dried overnight at 110° C., then calcined at 420° C. for 3 hours. The calcined product was cooled to room temperature and then ground to a 10–30 mesh size. This catalyst had a density of 0.297 gm/cc.

EXAMPLE 4

2% $Mo_{90}WCoK_{72}O_x$/98% $SiO_2$ 25 ml. of concentrated reagent grade $NH_4OH$ were dissolved in 25 ml. of distilled water. 2.0902 gms. of $(NH_4)_6Mo_7O_{24}.4H_2O$ were added to the mixture with stirring. 0.0333 gm. of $H_2WO_4$ was added. 0.0388 gm. of $Co(NO_3)_2.6H_2O$ was added. 0.9707 gm. of $KNO_3$ was added. The mixture was heated to a temperature of 95° C. and stirred rapidly for 15 minutes. 196.41 gms. of a 40% by weight colloidal dispersion of $SiO_2$ were added with stirring. The mixture was heated at boiling until near dryness. The mixture was then dried overnight at 110° C., then calcined at 420° C. for 3 hours. The calcined product was cooled to room temperature and then ground to a 10–30 mesh size. This catalyst had a density of 0.264 gm/cc.

EXAMPLE 5

2% $Mo_{90}WCoK_{10}O_x$/98% $SiO_2$ 25 ml. of concentrated reagent grade $NH_4OH$ were dissolved in 25 ml. of distilled water. 2.0902 gms. of $(NH_4)_6Mo_7O_{24}.4H_2O$ were added to the mixture with stirring. 0.0333 gm. of $H_2WO_4$ was added. 0.0388 gm. of $Co(NO_3)_2.6H_2O$ was added. 0.1348 gm. of $KNO_3$ was added. The mixture was heated to a temperature of 95° C. and stirred rapidly for 15 minutes. 134.56 gms. of a 40% by weight colloidal dispersion of $SiO_2$ were added. The mixture was heated at boiling until near dryness. The mixture was then dried overnight at 110° C., then calcined at 420° C. for 3 hours. The calcined product was cooled to room temperature and then ground to a 10–30 mesh size. This catalyst had a density of 0.268 gm/cc.

EXAMPLE 6

2% $Mo_{90}WCoO_x$/98% $SiO_2$ 50 ml. of concentrated reagent grade $NH_4OH$ were dissolved in 50 ml. of distilled water. 4.2188 gms. of $(NH_4)_6Mo_7O_{24}.4H_2O$, 0.0776 gm. of $Co(NO_3)_2.6H_2O$, and 0.0666 gm. of $H_2WO_4$ were added. The mixture was stirred. 50 ml. of this mixture was pipetted into a beaker. 129.94 gms. of a 40% by weight colloidal dispersion of $SiO_2$ were added to the pipetted mixture with stirring until a gel was formed. The gel was dried overnight at 110° C., then calcined at 400° C. for 4.5 hours. The calcined product was cooled to room temperature and then ground to a 10–30 mesh size. This catalyst had a density of 0.285 gm/cc.

EXAMPLE 7

20% [2% $Mo_{90}WCoO_x$/98% $SiO_2$]80% Alundum 25 ml. of concentrated reagent grade $NH_4OH$ were dissolved in 25 ml. of distilled water. 2.0902 gms. of $(NH_4)_6Mo_7O_{24}.4H_2O$ were added to the mixture with stirring. 0.0309 gm. of $WO_3$ was added. 0.0100 gm of $Co(NO_3)_2.6H_2O$ was added. The mixture was heated to a temperature of 95° C. and stirred rapidly for 15 minutes. 129.94 gms. of a 40% by weight colloidal dispersion of $SiO_2$ were added with stirring. 34.65 gms. of $SiO_2$ were added with stirring. The mixture was heated at boiling until near dryness. The mixture was dried overnight at 110° C., then calcined at 420° C. for 3 hours. The calcined product was ground to a fine powder using a mortar and pestle. Five samples of the powdered catalyst material, each weighing 1.5265 gms., were prepared. 30.53 gms. of Alundum and 6.106 gms. of water were placed in a rotating drum for 10 minutes. The first sample of powdered catalyst was added to the mixture of Alundum and water and the rotation was continued for 10 minutes. The second, third, fourth and fifth samples of powdered catalyst were added at 10-minute intervals in the same manner. Rotation of the drum was continued for 10 minutes after the addition of the fifth sample with the result being the formation of a coated catalyst. The coated catalyst was dried overnight at 110° C., then calcined at 500° C. for three hours. This catalyst had a density of 0.744 gm/cc.

EXAMPLE 8

2% $Mo_{90}WCoO_x$/98% $SiO_2$ 25 ml. of concentrated reagent grade $NH_4OH$ were dissolved in 25 ml. of distilled water. 2.0902 gms. of $(NH_4)_6Mo_7O_{24}.4H_2O$ were added to the mixture with stirring. 0.0309 gm. of $WO_3$ was added. 0.0388 gm. of $Co(NO_3)_2.6H_2O$ was added. The mixture was heated to a temperature of 95° C. and stirred rapidly for 15 minutes. 129.94 gms. of a 40% by weight colloidal dispersion of $SiO_2$ were added with stirring. 34.65 gm. of $SiO_2$ were added with stirring. The mixture was heated at boiling until near dryness. The mixture was then dried overnight at 110° C., then calcined at 420° C. for 3 hours. The calcined product was cooled to room temperature and then ground to a 10–30 mesh size. This catalyst had a density of 0.301 gm/cc.

EXAMPLE 9

10% [2% $Mo_{90}WCoO_x$/98% $SiO_2$]90% Alundum 3.4833 gms. of the catalyst of Example 8 were ground to a fine powder of <325 mesh and divided into five equal samples, each weighing 0.6967 gms. 31.35 gms. of Alundum and 3.15 gms. of water were placed in a rotating drum for 10 minutes. One of the samples of ground catalyst was adding to the mixture of Alundum and water and the rotation was continued for 10 minutes. The second, third, fourth and fifth samples of catalyst were similarly added at 10-minute intervals. After addition of the fifth sample, rotation was continued for an additional 10 minutes with the result being the formation of a coated catalyst. The coated catalyst was dried overnight at 110° C., and then calcined at 500° C. for 3 hours. This catalyst had a density of 0.857 gm/cc.

EXAMPLE 10

2% $Mo_{90}WCoO_x$/98% $SiO_2$ 25 ml. of concentrated reagent grade $NH_4OH$ were dissolved in 25 ml. of distilled water. 2.0902 gms. of $(NH_4)_6Mo_7O_{24}.4H_2O$ were added to the mixture with stirring. 0.0388 gm. of $Co(NO_3)_2.6H_2O$ was added. 0.0309 gm. of $WO_3$ was added. The mixture was heated to a temperature of 95° C. and stirred rapidly for 15 minutes. 221.25 gms. of a 40% by weight colloidal dispersion of SiO$_2$ were added with stirring. The mixture was heated at boiling until near dryness. The mixture was placed in a filter and washed three times with benzene under a vacuum. The mixture was then dried overnight at 110° C., then calcined at 420° C. for 3 hours. The calcined product was cooled to room temperature and then ground to a 10–30 mesh size. This catalyst had a density of 0.504 gm/cc. This catalyst had a density of 0.248 gm/cc.

Process

In the process of the present invention methane is contacted with the molybdenum-tungsten-containing catalyst of the invention in the presence of oxygen under reaction conditions to form one or more higher order hydrocarbons. The higher order hydrocarbons may subsequently be further processed if necessary to provide desired hydrocarbon products.

The present invention is particularly suitable for converting methane to ethane, ethylene or mixtures of ethane and ethylene. Natural gas which, as discussed above, generally contains a major amount of methane, can be treated in accordance with the inventive method. The other materials generally present in natural gas such as other hydrocarbons (e.g., ethane, propane, the butanes, the pentanes, etc.), water, carbon dioxide, nitrogen, carbon monoxide and inert gases generally do not affect the efficiency of the inventive method.

The process of the present invention is an oxidative reaction. Gaseous oxygen may be provided as substantially pure oxygen or diluted with nitrogen, carbon dioxide, carbon monoxide, or other inert gases (e.g., Nobel gases such as helium, neon, argon, etc.), or may be provided in air. Preferably the gaseous reactant contains from about 50% to about 90% by volume of methane. The mole ratio of oxygen to methane preferably ranges from about 0.1 to about 1 mole of oxygen per mole of methane, more preferably from about 0.1 to about 0.5 mole of oxygen per mole of methane, more preferably from about 0.1 to about 0.3 mole of oxygen per mole of methane, more preferably about 0.2 mole of oxygen per mole of methane. The gaseous reactant can contain from zero up to about 25 moles of nitrogen and/or other inert gases (e.g., Nobel gases such as helium, neon, argon, etc.), per mole of methane. The gaseous reactant can also contain from zero up to about 25 moles of water per mole of methane.

The catalyst can be regenerated by passing oxygen over it at an elevated temperature. Preferably a mixture of oxygen and an inert gas (e.g., air) is passed over the catalyst at the reaction temperature for a sufficient period of time (e.g., 15 minutes) to reoxidize the catalyst. An advantage of the inventive process is, however, that regeneration is not required or at least not required as often as with processes that do not employ oxygen in the feedstream.

The inventive process can be carried out by contacting the gaseous reactant with one of the catalysts described above in a fluid bed reactor, fixed bed reactor or any other suitable reactor configuration such as a moving bed reactor, swing reactor system or membrane reactor. The reaction can be conducted in a continuous or a batch-type mode. The reaction temperature is preferably in the range of from 250° C. to about 1000° C., more preferably from about 500° C. to about 750° C., more preferably from about 550° C. to about 650° C.

The average contact time of the reactants with the catalyst is dependent upon the degree of reaction that is desired. When the desired product is ethane, ethylene or mixtures thereof, the contact time is preferably from about 0.2 seconds to about 1.2 seconds, more preferably from about 0.5 seconds to about 0.9 seconds. However, average contact times in the range of from about 0.05 to about 20 seconds can be employed under various advantageous circumstances.

The reaction can be conducted at a pressure that can be in the range of from atmospheric pressure up to about 10,000 psig, but is preferably in the range of from about 400 to about 1000 psig., more preferably in the range of from about 500 to about 800 psig.

Products of methane conversion in accordance with the present invention include ethane, ethylene and higher order hydrocarbons as well as by-product water, carbon monoxide and carbon dioxide. Unconverted methane can be recycled to the reaction so as to increase the overall yield of higher order hydrocarbons by this process.

If the reaction contemplates recycling the unreacted natural gas, then the portion of the feed stream containing minor amounts of the ethane, propane, butane and pentane may change, depending on the efficiency of the product recovery apparatus. These alkanes need not be fully removed from the reactor feed stream.

The higher order hydrocarbons may be easily transported and have versatile applications in chemical processing as well as uses as fuels. In addition, these higher order hydrocarbons may be further processed to form substantially liquid hydrocarbons. The term "substantially liquid hydrocarbons" refers to hydrocarbons that are primarily in the liquid state at a temperature of 25° C. and a pressure of one atmosphere. For example, in U.S. Pat. No. 4,100,218, ethane is subjected to thermal cracking at temperatures of from about 815° C. to about 875° C. to produce an olefin-rich effluent which is then cooled to a temperature between about 315° C. and about 650° C. and contacted with a zeolite so as to produce a liquid hydrocarbon product suitable for use as LPG, gasoline and/or aromatics concentrate. In U.S. Pat. No. 4,120,910, ethane is converted to liquid aromatic compounds with a process which comprises contacting, in the absence of added air or oxygen under conversion conditions, a gaseous paraffinic hydrocarbon feed containing ethane, with a catalyst comprising a crystalline aluminosilicate zeolite characterized by a constraint index within the approximate range of 1 to 12 and a silica to alumina ratio of at least 12, said catalyst having incorporated therein from about 0.01 to 30 weight percent based on the total weight of the catalyst of a metal or metal oxide wherein said metal is selected from the group consisting of Group VIII, IIB and IB metals and mixtures thereof whereby ethane present in said gaseous feed is converted to aromatic compounds and recovering said aromatic compounds as liquids. U.S. Pat. Nos. 4,100,218 and 4,120,910 are incorporated herein by reference.

Other known processes are also available for the conversion of ethane and ethylene to ethanol, ethylene glycol, polyethylene, and other chemicals useful as fuels, fuel additives and lubricants. Thus, the process disclosed herein for upgrading methane to higher order hydrocarbons may be integrated with additional process steps for converting such hydrocarbons to other useful chemicals.

Advantages over previously disclosed processes for the conversion of methane to higher order hydrocarbons include higher selectivities to higher molecular weight hydrocarbons, higher conversion rates, longer catalyst life and avoidance of corrosive and/or expensive gas phase promoters. The use of feedstreams containing oxygen (e.g., air) permits the use of simplified process techniques in comparison to those processes that avoid the use of oxygen in their feedstream.

a gas chromatograph. Liquid was collected, weighed and injected into two gas chromatographs for analysis. Formaldehyde was detected by thermal conductivity. The presence of methanol and other oxygenates was determined by flame ionization.

The results are indicated in Table I.

TABLE I

| Test Run | A | B | C | D | E | F | G | H | I |
|---|---|---|---|---|---|---|---|---|---|
| Catalyst (Example No.) | 1 | 1 | 2 | 3 | 4 | 5 | 6 | 7 | 7 |
| Temp. (°C.) | 550 | 550 | 550 | 550 | 550 | 550 | 550 | 650 | 650 |
| Pressure (PSIG) | 520 | 520 | 800 | 520 | 520 | 520 | 800 | 520 | 520 |
| Contact Time (sec) | 7.954 | 1.664 | 0.474 | 1.003 | 1.343 | 0.658 | 0.472 | 0.860 | 0.850 |
| Gas Velocity, (cm/sec) | 2.716 | 12.987 | 19.525 | 9.229 | 9.194 | 18.764 | 19.601 | 21.545 | 21.790 |
| Conversion (%) | 17.19 | 12.35 | 8.97 | 9.11 | 11.59 | 9.26 | 9.59 | 6.03 | 13.21 |
| Feed Stream (% Vol.) | | | | | | | | | |
| Methane | 49.37 | 10.33 | 8.23 | 17.69 | 17.53 | 6.17 | 8.02 | 8.57 | 8.47 |
| Nitrogen | — | 43.98 | 53.80 | 69.94 | 70.01 | 34.19 | 54.23 | 34.08 | 32.46 |
| Air | 50.63 | 10.59 | 5.66 | 12.37 | 12.46 | 6.17 | 5.57 | 5.86 | 8.13 |
| Water | — | 35.10 | 32.31 | — | — | 51.12 | 32.18 | 51.49 | 50.93 |
| Product* (% Vol.) | | | | | | | | | |
| Ethane | 13.44 | 13.96 | 15.11 | 9.34 | 13.44 | 16.14 | 14.39 | 23.78 | 14.88 |
| Ethylene | 5.75 | 9.11 | 4.37 | 2.99 | 5.75 | 8.07 | 3.51 | 16.36 | 19.89 |
| CO | 64.27 | 46.81 | 63.44 | 73.10 | 64.27 | 57.02 | 64.77 | 42.94 | 50.98 |
| $CO_2$ | 11.95 | 23.21 | 4.72 | 9.50 | 11.95 | 5.16 | 4.29 | 3.63 | 7.67 |
| $C_1$–$C_3$ oxygenated hydrocarbons** | 4.51 | 6.91 | 12.13 | 5.06 | 4.58 | 13.62 | 13.04 | 13.30 | 6.57 |

| Test Run | J | K | L | M | N | O | P | Q |
|---|---|---|---|---|---|---|---|---|
| Catalyst (Example No.) | 7 | 7 | 8 | 8 | 8 | 8 | 9 | 10 |
| Temp. (°C.) | 650 | 650 | 550 | 550 | 550 | 550 | 550 | 610 |
| Pressure (PSIG) | 520 | 520 | 520 | 520 | 520 | 520 | 520 | 800 |
| Contact Time (sec) | 0.849 | 0.623 | 2.552 | 0.712 | 0.637 | 1.349 | 0.653 | 0.407 |
| Gas Velocity, (cm/sec) | 21.808 | 29.720 | 8.466 | 17.340 | 19.377 | 9.149 | 18.905 | 22.729 |
| Conversion (%) | 13.56 | 5.08 | 15.05 | 9.74 | 11.36 | 13.93 | 6.83 | 8.39 |
| Feed Stream (% Vol.) | | | | | | | | |
| Methane | 8.39 | 6.23 | 17.44 | 8.34 | 8.41 | 16.56 | 8.50 | 7.31 |
| Nitrogen | 31.63 | 49.90 | 64.99 | 33.28 | 33.01 | 67.24 | 34.43 | 49.62 |
| Air | 9.05 | 6.55 | 17.58 | 8.29 | 8.22 | 16.20 | 5.88 | 4.98 |
| Water | 50.86 | 37.32 | — | 50.08 | 50.35 | — | 51.18 | 38.08 |
| Product* (% Vol.) | | | | | | | | |
| Ethane | 13.87 | 30.57 | 14.46 | 15.46 | 15.65 | 15.04 | 16.52 | 17.76 |
| Ethylene | 18.45 | 11.44 | 8.84 | 9.47 | 9.32 | 9.53 | 9.80 | — |
| CO | 54.26 | 41.74 | 66.33 | 57.26 | 59.23 | 64.43 | 53.76 | 65.13 |
| $CO_2$ | 7.71 | — | 8.76 | 7.15 | 5.73 | 8.00 | 6.56 | 4.72 |
| $C_1$–$C_3$ oxygenated hydrocarbons** | 5.74 | 16.26 | 1.60 | 10.67 | 10.08 | 2.99 | 13.36 | 12.40 |

*Analysis excludes water, hydrogen, oxygen, nitrogen and methane.
**Mixture of one or more of methanol, ethanol, propanol, formaldehyde, acetaldehyde and acetic acid.

In order to further illustrate the inventive process, the following test results are provided. A high-pressure, fixed-bed 20 cc. reactor was used. The flow of methane air, and nitrogen gases were controlled by flow controllers. These were calibrated for high pressure (600 lbs.) and high flow rates (0–5000 cc/min.). The water flow rate was controlled by a minipump, which is calibrated for 0.48–4.80 ml/min. Methane, nitrogen, air, and steam entered the reactor through a ¼-inch stainless steel feed line. The gases were preheated to approximately 420° C. before entering the reactor. The effluent gases from the reactor were cooled when they pass through a 5-inch condenser. A 5-way valve then directed the flow to one of four collecting vessels; each capable of holding 150 cc. of liquid sample. The collectors were supported in a steel "ice bath". After the liquid products condensed in the collector, the effluent gas flowed through a back pressure regulator, through a gas gun, to a flow measuring device. Each experimental run was 30 minutes with a 10 minute pre-run. Gas samples were taken at 15 and 25-minutes; the flow rate was measured before each sample. The gas samples were analyzed by While the invention has been explained in relation to its preferred embodiments, it is to be understood that various modifications thereof will become apparent to those skilled in the art upon reading this specification. Therefore, it is to be understood that the invention disclosed herein is intended to cover such modifications as fall within the scope of the appended claims.

I claim:

1. A catalyst comprising a molybdenum-tungsten-containing complex represented by the formula

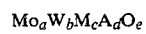

$$Mo_a W_b M_c A_d O_e$$

wherein
M is selected from the group consisting of one or more metals selected from any of Groups IB, IIB, IVB, VB or VIII of the Periodic Table and/or one or more of Y, Cr, Mn, Re, B, In, Ge, Sn, Pb, Th or U, or a mixture of two or more of the metals in said group;

A is at least one metal selected from the group consisting of alkali metals, alkaline earth metals, Lanthanide series metals, Tl, or a mixture of two or more of the metals in said group;

a is a number in the range of from about 1 to about 200;

b is a number in the range of from about 1 to about 200;

with the proviso that either Mo or W is in excess of the other, the ratio of a:b being about 90:1 or about 1:90 1:4;

c is a number such that the ratio of c:(a+b) is in the range of from 0:100 to about 10:100;

d is a number such that the ratio of d:(a+b) is in the range of from 0:100 to about 75:100; and e is the number of oxygens needed to fulfill the valence requirements of the other elements.

2. The catalyst of claim 1 wherein M is selected from the group consisting of Co, V, Re, Nb, Rh, Ir, Ag, B, Ru, Pt, U, Th, Ti or a mixture of two or more thereof.

3. The catalyst of claim 1 wherein M is selected from the group consisting of Co, V, Re, Nb or a mixture of two or more thereof.

4. The catalyst of claim 1 wherein A is selected from the group consisting of Na, K, Rb, Cs, Mg, Ca, Sr, Ba or a mixture of two or more thereof.

5. The catalyst of claim 1 wherein A is selected from the group consisting of K, Na, Cs or a mixture of two or more thereof.

6. The catalyst of claim 1 wherein a is in the range of from about 1 to about 100.

7. The catalyst of claim 1 wherein b is in the range of from about 1 to about 100.

8. The catalyst of claim 1 wherein the ratio of c:(a+b) is in the range of from about 1:100 to about 5:100.

9. The catalyst of claim 1 wherein the ratio of c:(a+b) is in the range of from about 1:100 to about 2:100.

10. The catalyst of claim 1 wherein the ratio of d:(a+b) is in the range of from about 1:100 to about 30:100.

11. The catalyst of claim 1 wherein the ratio of d:(a+b) is in the range of from about 2:100 to about 10:100.

12. The catalyst of claim 1 wherein said molybdenum-tungsten-containing complex is supported on a carrier.

13. The catalyst of claim 12 wherein said carrier is silica, alumina, fused alumina, zirconia, hafnia, titania, magnesia, germanium oxide, silicon carbide, clay, zeolite or activated carbon.

14. The catalyst of claim 12 wherein said carrier comprises silica.

15. The catalyst of claim 1 wherein said molybdenum-tungsten-containing complex is supported on a carrier, said catalyst being prepared by the steps of (1) preparing a powdered precipate of said molybdenum-tungsten-containing complex, (2) preparing a wetted carrier, and (3) contacting said wetted carrier with said prrecipitate until said catalyst is formed.

* * * * *